US006270744B1

(12) United States Patent
Iwasaki et al.

(10) Patent No.: US 6,270,744 B1
(45) Date of Patent: Aug. 7, 2001

(54) DIAGNOSTIC AGENT FOR ANGIOPATHIC DISEASES

(75) Inventors: Tsutomu Iwasaki; Ryozo Nagai, both of Maebashi; Hirohisa Katoh, Choshi, all of (JP)

(73) Assignee: Yamasa Corporation, Chiba (JP)

( * ) Notice: Subject to any disclaimer, the term of this patent is extended or adjusted under 35 U.S.C. 154(b) by 0 days.

(21) Appl. No.: 09/125,430

(22) PCT Filed: Feb. 19, 1997

(86) PCT No.: PCT/JP97/00435

§ 371 Date: Jan. 4, 1999

§ 102(e) Date: Jan. 4, 1999

(87) PCT Pub. No.: WO97/29784

PCT Pub. Date: Aug. 21, 1997

(30) Foreign Application Priority Data

Feb. 19, 1996 (JP) .................................................... 8-055512
Mar. 18, 1996 (JP) .................................................... 8-090034

(51) Int. Cl.⁷ ............................ A61K 51/00; A61M 36/14
(52) U.S. Cl. ...................... 424/1.49; 424/1.11; 424/1.53; 424/9.1; 424/141.1; 435/7.94
(58) Field of Search ................... 424/1.11, 1.65, 424/1.53, 1.49, 141.1, 9.1, 130.1; 530/387.1, 387.2; 206/223, 569, 570; 534/7, 10–16; 435/7.94

(56) References Cited

U.S. PATENT DOCUMENTS

| 4,767,843 | * | 8/1988 | Yazaki et al. | 530/387 |
| 4,943,427 | * | 7/1990 | Yazaki et al. | 424/1.11 |
| 5,046,499 | | 9/1991 | Berger . | |
| 5,626,830 | * | 5/1997 | Sikorska et al. | 424/1.49 |
| 5,747,652 | * | 5/1998 | Nagai et al. | 530/387.9 |
| 5,908,757 | * | 6/1999 | Katoh et al. | 435/7.94 |

FOREIGN PATENT DOCUMENTS

| 0 417 191 | | 5/1989 | (EP) . |
| 0 443 511 | | 2/1991 | (EP) . |
| 60-201260 | | 10/1985 | (JP) . |
| 2219596 | | 9/1990 | (JP) . |
| 3-504499 | | 10/1991 | (JP) . |
| 5148160 | | 6/1993 | (JP) . |
| 5-176790 | | 7/1993 | (JP) . |
| 90 11520 | * | 10/1990 | (WO) . |
| 90/11520 | | 10/1990 | (WO) . |
| 89/12467 | | 12/1991 | (WO) . |
| 96/12507 | | 5/1996 | (WO) . |
| 96 12507 | * | 5/1996 | (WO) . |

* cited by examiner

Primary Examiner—Dameron L. Jones
(74) Attorney, Agent, or Firm—Wenderoth, Lind & Ponack, L.L.P.

(57) ABSTRACT

A diagnostic agent for angiopathic diseases containing a monoclonal antibody against human smooth muscle myosin or active fragments of the antibody labeled with a radioactive isotope; a kit thereof; and a method of diagnostic imaging for angiopathic diseases by using the same. The invention permits the diagnostic imaging of angiopathic diseases such as dissecting aortic aneurysm and angiitis and the specification of the region affected by these diseases.

6 Claims, 4 Drawing Sheets

Distribution of $^{125}$I-Anti-Smooth Muscle Myosin Antibody (Fab) in Rat under double column heading as US 6,270,744 B1

DIAGNOSTIC AGENT FOR ANGIOPATHIC DISEASES

This application is a 371 of PCT/JP97/00435 filed Feb. 19, 1997.

BACKGROUND OF THE INVENTION

1. Technical Field

The present invention relates to a diagnostic agent useful for diagnostic imaging for angiopathic diseases such as dissecting aortic aneurysm (also called aortic dissection) and angiitis, and to a kit for diagnosis.

2. Description of the Related Art

The onset mechanism of dissecting aortic aneurysm includes partial breakage of intima of an aorta, flow of blood from a formed hiatus to media to cause dissection of a vascular wall, and necrosis of vascular smooth muscle cells. Grave cases bring strong pectralgia and a high fatality rate. As onset factors for these diseases, there are indicated hypertension, as well as degeneration and fragility-increase of media caused by arterial sclerosis and cystic medial necrosis.

Meanwhile, angiitis is caused by a factor such as collagen disease, and a lesion thereof often extends blood vessels of the whole body accompanied by necrosis of vascular smooth muscle cells and induces a grave fatal complication such as DIC (disseminated intravascular coagulation), thrombosis, or embolism.

Thus, many angiopathic diseases accompanied by necrosis of vascular smooth muscle cells, such as dissecting aortic aneurysm or angiitis, are grave diseases and therefore a speedy and accurate diagnosis is needed for effective medical treatment and prevention of complications.

Conventionally, these angiopathic diseases have been diagnosed only through morphological diagnosis conducted by diagnostic imaging or on the basis of abnormal values of general biological blood tests attributed to a primary disease, since there exist no specific test methods for these diseases. Thus, diagnosis of angiopathic diseases has confronted great difficulties.

Among these diagnosis methods, there are utilized echography, CT (X-ray computer tomography), DSA (digital subtraction angiography), MRI (magnetic resonance imaging), and aortography used as a method for diagnosing dissecting aortic aneurysm similar to that for diagnosing other heart diseases. Of these, DSA and aortagraphy are dangerous test methods in an acute stage of the diseases due to considerable invasiveness. In contrast, diagnostic imaging including echography, CT, and MRI, although less dangerous even in an acute stage, generally yields a morphological diagnosis, which is not able to distinguish between an old inveterate lesion and a new lesion in an acute stage. Thus, the above diagnostic imaging is not able to specifically diagnose a pathological region in an acute stage at which vascular smooth muscle cells are being damaged.

Meanwhile, a method for diagnosing angiitis through conventional diagnostic imaging is more difficult than that for diagnosing dissecting aortic aneurysm, since angiitis itself is a disease accompanied by no characteristic morphological changes.

Therefore, an object of the present invention is to develop a tracer preparation to enable accurate diagnostic imaging for a region affected by these diseases by binding specifically to vascular smooth muscle cells damaged at an acute stage of dissecting aortic aneurysm or angiitis.

SUMMARY OF THE INVENTION

The present inventors have conducted earnest studies to achieve the above object, and have found that smooth muscle myosin serving as a primary protein in blood vessels is useful for diagnostic imaging for angiopathic diseases such as dissecting aortic aneurysm and angiitis, particularly in an acute stage. The present invention was accomplished based on this finding.

Accordingly, the present Invention provides a diagnostic agent for angiopathic diseases containing a monoclonal antibody against human smooth muscle myosin or active fragments of the antibody labeled with a radioactive isotope. The present invention also provides a kit for diagnosing angiopathic diseases comprising a coupling compound formed of a bifunctional chelating agent and either a monoclonal antibody against human smooth muscle myosin or active fragments of the antibody, and a solution of radioactive isotopes.

Furthermore, the present invention provides a method of diagnostic imaging for angiopathic diseases by use of the above diagnostic agent or kit.

DESCRIPTION OF THE PREFERRED EMBODIMENTS

Figure 1:
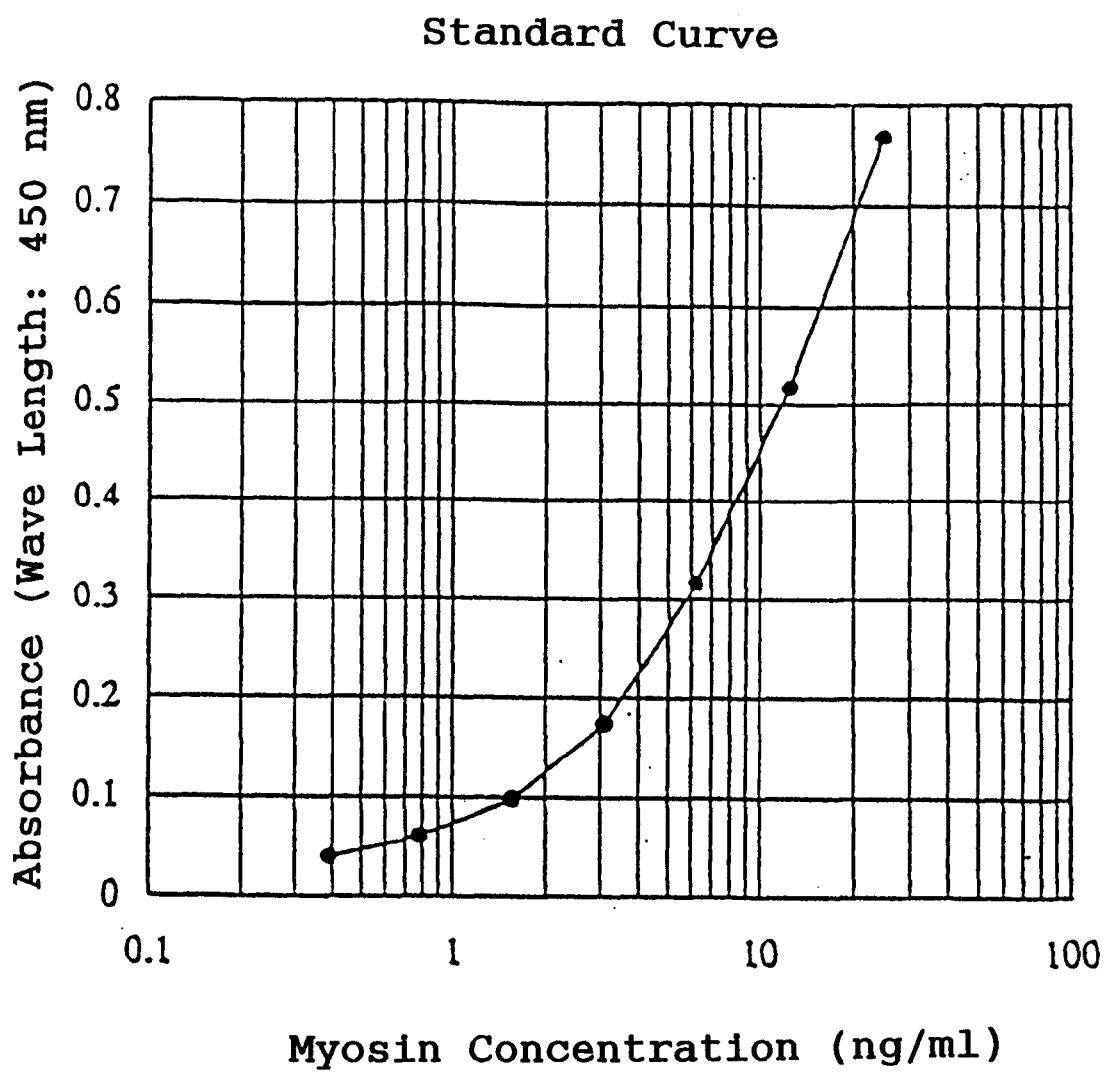
FIG. 1 shows the standard curve.

The diagnostic agent of the present invention is used to perform proper and accurate diagnostic imaging for a region affected by angiopathic diseases by binding a monoclonal antibody against human smooth muscle myosin or active fragments of the antibody labeled with a radioactive isotope, specifically to the region affected by these diseases. Therefore, the diagnostic agent must contain at least a monoclonal antibody against human smooth muscle myosin or active fragments of the antibody labeled with a radioactive isotope.

No particular limitation is imposed on the monoclonal antibody used in the present invention so long as it specifically binds to human smooth muscle myosin, particularly to a heavy chain of human smooth muscle myosin, and there is preferably used a monoclonal antibody having low cross-reactivity to other types of myosin.

Such a monoclonal antibody may be prepared by employing a known method shown in the below-described Examples (See, e.g., "*Men-eki Seikagaku Kenkyuhou* (*Zoku-Seikagaku Jikken Kouza* 5)," Edited by The Biochemical Society of Japan, pages 1–88 (1986); Biochemistry, 27, 3807–3811 (1988); Eur. J. Biochem., 179, 79–85 (1989); J. Mol. Biol., 198, 143–157 (1987); J. Biol. Chem., 264, 9734–9737 (1989); J. Biol. Chem., 264, 18272–18275 (1989); J. Biol. Chem., 266, 3768–3773 (1991); and Circulation, 88, 1804–1810 (1993)).

As the monoclonal antibodies, a monoclonal antibody itself or active fragments of the monoclonal antibody may be used. No particular limitation is imposed on the active fragments; there may be used any of a variety of fragments such as F(ab')$_2$, Fab', or Fab, so long as it has characteristics of the monoclonal antibody of the present invention. By use of such active fragments, the half-life may be reduced and in vivo clearance may increase.

Such active fragments may be prepared by employing a known method such as papain-, pepsin-, or tripsin-treatment to a purified monoclonal antibody (See, "*Men-eki Seikagaku Kenkyuhou* (*Zoku-Seikagaku Jikken Kouza* 5)," Edited by The Biochemical Society of Japan, page 89 (1986)).

The thus-prepared monoclonal antibody or active fragments may be used as a diagnositic agent of the present invention by labeling with radioactive isotopes.

In the present invention, examples of the radioactive isotopes include iodine-125, iodine-123, iodine-131, indium-111, indium-113m, technetium-99m, gallium-67, lead-203, ruthenium-97, mercury-197, thallium-201, and bismuth-212.

The labeling method may be selected from among a variety of known methods in accordance with the employed nuclear species, and examples include a direct labeling of the antibody or active fragments with radioactive isotopes, such as a chloramine T method or a lactoperoxidase method, and a method involving bonding a bifunctional chelating agent to the antibody or active fragments to form a covalent bond and labeling the formed coupling compound with the above nuclear species.

Examples of the bifunctional chelating agents used in the present invention include 1-amino-6,17-dihydroxy-7,10,28, 21-tetraoxo-27-(N-acetylhydroxyimino)-6,11,17,22-tetrazaheptaeicosane (despherioxamine), 8-hydroxyquinoline, ethylenediaminetetraacetic acid, diethylenetriaminepentaacetic acid (DTPA), and diaminocyclohexyltetraacetic acid, and these chelating agents and the antibody or active fragments are bonded by a customarily employed method such as a carbodiimide method, an acid anhydride method, or a glutaraldehyde method.

The kit for the diagnosis of the present invention is used to prepare a monoclonal antibody against human smooth muscle myosin or active fragments of the antibody labeled with a radioactive isotope; in order to perform accurate diagnostic imaging for a region affected by angiopathic diseases by binding the labeled monoclonal antibody or active fragments of the antibody specifically to the region affected by these diseases. Therefore, the kit for the diagnosis must be fabricated so as to enable the preparation of at least a monoclonal antibody against human smooth muscle myosin or active fragments of the antibody labeled with a radioactive isotope. In one specific embodiment, there may be exemplified a kit containing a coupling compound comprising a bifunctional chelating agent and either a monoclonal antibody against human smooth muscle myosin or active fragments of the antibody, as well as a solution of radioactive isotopes.

The diagnostic agent and kit of the present invention may contain, in addition to the above reagents, a chromatographic column to purify nuclear species; a carrier such as a sodium chloride solution or a glucose solution to prepare into a form of administration; other stabilizers; etc.

The diagnostic agent of the present invention is administered to the human body through intravenous injection. Therefore, the diagnostic agent of the present invention is used in a form suitable for intravenous injection by use of the above-mentioned carrier, etc. The diagnostic agent of the present invention is usually administered in an amount of 100 $\mu$Ci-30 mCi, preferably 500 $\mu$Ci-3 mCi, depending on the radioactive isotope used for labeling.

The diagnostic imaging by use of the diagnostic agent of the present invention may be performed as follows. One to 48 hours after administration of the agent of the present invention, a region such as a region of the patient's heart where angiopathic disorders seem to be generated is scanned by autoradiography, or by use of a scintillation scanner or a scintillation camera, to thereby detect radioactivity attributed to the agent of the present invention and to depict the image thereof.

EXAMPLES

The present invention will next be described in detail by way of examples, which should not be construed as limiting the invention.

Example 1
(Preparation of myosins)

Human uterus smooth muscle myosin, human aorta smooth muscle myosin, human small intestine smooth muscle myosin, human platelet myosin, and human skeletal muscle myosin were provided by Dr. Matsumura, Saga Medical College. Human cardiac muscle myosin was purified according to the method of Yazaki (Circ. Res., 36:208, 1975). For each type of myosin, purity was assessed by SDS-PAGE, and then the concentration of protein was determined according to the method of Lawry (J. Biol. Chem., 193:265–275, 1951) using bovine serum albumin as a standard. Example 2
(Preparation of monoclonal antibodies)
1) Preparation of monoclonal antibody-producing hybridomas BALB/c mice aged 6 to 8 weeks were immunized intraperitoneally with 25 to 50 $\mu$g of human uterus smooth muscle myosin emulsified with Freund's complete adjuvant, 4 to 7 times at 2 to 4 weeks interval, after which human uterus smooth muscle myosin (10 $\mu$g) was administered by intravenous injection.

The spleen of each mouse was removed three days after the final immunization, and the spleen cells and mouse myeloma cells P3×63Ag8U.1(P3U1) (ATCC CRL-1597) were mixed at a ratio of 10:1. An RPMI 1640 solution (1 ml) containing 50% polyethylene glycol was gradually added to pellets obtained by centrifugal separation of the mixture to thereby conduct cell fusion. Subsequently, an RPMI 1640 culture medium was added thereto to adjust the volume to 10 ml and the mixture was centrifuged to thereby obtain pellets, which were suspended in an RPMI 1640 culture medium containing 10% fetal calf serum at the concentration of P3U1 3×10$^4$ cells/0.1 ml. The suspension was dispensed to a 96-well microplate in an amount of 0.1 ml/well.

After one day an HAT culture medium (0.1 ml) was added to each well, and half of the medium was replaced with fresh HAT medium every 3–4 days.

The culture supernatant was sampled 7–10 days after fusion, dispensed in an amount of 50 $\mu$l/well into a 96-well polyvinyl chloride (PVC) plate which had been precoated with human uterus smooth muscle myosin and blocked with 3% gelatin, and allowed to react at room temperature for one hour. After three washings with PBS, a solution containing biotinylated horse anti-mouse IgG (Vector Co.) diluted 500 times With PBS containing 1% bovine serum albumin (BSA) was added in an amount of 50 $\mu$l/well and the microplate was allowed to stand at room temperature for one hour. After three washings with PBS, a solution containing peroxidase-avidin D (Vector Co.) diluted 2000 times with PBS containing 1% BSA was added in an amount of 50 $\mu$l/well and the microplate was allowed to stand at room temperature for 15 minutes. After three washings with PBS, 200 µl of a substrate solution (4-aminoantipyrine, 0.25 mg/ml, phenol, 0.25 mg/ml, 0.4 M hydrogen peroxide) was added thereto and the mixture was subjected to coloration at room temperature. The absorbance at 550 nm was measured by use of a microplate photometer, to thereby select hybridomas producing monoclonal antibodies reacting specifically with human uterus smooth muscle myosin.

The thus-selected hybridomas were subjected to cloning by limiting dilution and there were established five strains of hybridoma (1H6, 4E12, 9A12, 9D7, 10G2) against human uterus smooth muscle myosin. The number of specific antibody-positive wells, growth wells, and the total number of wells are shown in Table 1. Of the selected hybridomas, hybridoma 1H6 and hybridoma 4E12 were deposited with the National Institute of Bioscience and Human-Technology, Agency of Industrial Science and Technology (1–3, Higashi 1 chome, Tsukuba-shi, Ibaraki-ken, 305, JAPAN) as SMHMW 1H6 and SMHMW 4E12 on Oct. 13, 1994 under Budapest Treaty, and were allotted accession numbers FERM BP-4829 and FERM BP-4830 dated Oct. 13. 1994.

TABLE 1

| Wells which indicated positive to specific antibody | Wells which indicated growth | Total No. of wells |
|---|---|---|
| 11 | 653 | 940 |

2) Preparation and purification of monoclonal antibodies

Next, cells of each hybridoma established were cultured and then intraperitoneally administered to mice previously given pristane, in number of $3\times10^6$ per mouse. About two weeks after the administration of hybridomas, 5 ml of ascites was collected from each mouse.

The ascites was mixed with an equal volume of 1.5 M glycine-hydrochloric acid buffer (pH 8.9) containing 3 M sodium chloride, and was passed through a Protein A Sepharose CL-4B (Pharmacia Co.) equilibrated with the same buffer as above. After the column was washed with a sufficient amount of the same glycine-hydrochloric acid buffer, the antibody was eluted with 0.1 M citrate buffer (pH 6.0). The eluate was dialyzed against PBS, and purity was confirmed by SDS-polyacrylamide gel electrophoresis (SDS-PAGE) to thereby obtain a purified monoclonal antibody.

Example 3
(Properties of the monoclonal antibodies)
1) Isotype

The culture supernatant of each hybridoma was dispensed into a 96-well PVC plate which had been precoated with human uterus smooth muscle myosin and blocked with 3% gelatin, and the isotype of antibodies was determined with MonoAb-ID EIA kit (Zymed Co.). The results are shown in Table 2.

TABLE 2

| Hybridoma | 1H6 | 4E12 | 9A12 | 9D7 | 10G2 |
|---|---|---|---|---|---|
| Isotype | IgG1/κ | IgG1/κ | IgG1/κ | IgG1/κ | IgG1/κ |

2) Specificity analysis by Western blotting

The specificities of monoclonal antibodies were analyzed by Western blotting.

Human uterus smooth muscle myosin (1 mg/ml) was mixed with an equal volume of a reducing solution and the mixture was heated at 100° C. for five minutes. SDS-PAGE was performed with a mini-gel electrophoresis apparatus (Marysal Co.) using a 10% separated gel and a 5% concentrated gel at 10 mV for approximately three hours. Blotting was performed with a blotting apparatus for mini-gel (Marysal Co.) at 37 V for about 18 hours to transcribe protein to a nitrocellulose membrane, which was subsequently cut along electrophoresis lines into strips. Some of them were treated with Amido Black to stain protein and the remainder were blocked with 3% gelatin and then reacted with a culture supernatant of each hybridoma at room temperature for one hour.

Subsequently, the reaction mixture was washed twice for 10 minutes each time with 20 mM Tris-500 mM NaCl (pH 7.5) buffer containing 0.05% Tween 20(T-TBS) and reacted with 500 fold-diluted biotinylated horse anti-mouse IgG (Vector Co.) at room temperature for one hour. The reaction mixture was then washed twice with T-TBS for 10 minutes and reacted with 2000 fold-diluted peroxidase-avidin D (Vector Co.) at room temperature for 15 minutes. The reaction mixture was then washed twice with T-TBS for 10 minutes, treated with a color development solution (containing 30 mg of HRP color development reagent (Bio-Rad Co.), 10 ml of methanol, 50 ml of TBS and 30 µl of a 30% hydrogen peroxide), and then washed with distilled water.

When protein-staining was performed using Amido Black, there were observed five bands, i.e., 200K (uterus smooth muscle myosin heavy chain), 140K (fragment of uterus smooth muscle myosin heavy chain), 70K (fragment of uterus smooth muscle myosin heavy chain), 20K (uterus smooth muscle myosin light chain), and 17K (uterus smooth muscle myosin light chain). It was confirmed that all antibodies reacted with a human uterus smooth muscle myosin heavy chain and did not react with a light chain thereof.

3) Cross-reactivity analysis by use of a sandwich method
a) Preparation of biotinylated antibodies Each of the above monoclonal antibodies was dialyzed against a 0.1 M sodium hydrogencarbonate solution, and the dialyzed solution was concentrated to 2 mg/ml by use of a Centriflow (Amicon Co.). Biotin (Long-arm) NHS reagent (Vector Co.) was dissolved in dimethylformamide to a concentration of 10 mg/ml, of which 20 µl was mixed with the above antibody solution (1 ml). The mixture was allowed to react at room temperature for two hours. After addition of ethanolamine (5 µl) to terminate reaction, the mixture was dialyzed twice against PBS, to thereby obtain a biotinylated antibody. The biotinylated antibody was diluted to 1 µg/ml with PBS containing 1% BSA, to thereby obtain a solution of the biotinylated antibody.

b) Preparation of immobilized antibodies

An anti-smooth muscle myosin monoclonal antibody (4E12) was diluted with PBS to 10 µg/ml and dispensed into a 96-well plate (H type: Sumitomo Bakelite Co., Ltd.) in an amount of 50 µl/well, and the microplate was allowed to stand at 40° C. overnight. After the antibody was washed three times with PBS containing 0.05% Tween 20, 0.5% skim milk was dispensed thereto in an amount of 300 µl/well and the plate was allowed to stand at room temperature for one hour. The skim milk solution was removed to thereby obtain an immobilized antibody reagent.

c) Preparation of other reagents and preparation of kits
* Standard solutions of smooth muscle myosin;

To prepare the standard solutions, human aortic smooth muscle myosin was diluted with PBS containing 1% BSA to attain a concentration of 25, 12.5. 6.25, 3.125, 1.563, 0.781, or 0.391 ng/ml.

* Washing solution;

To prepare the solution, Tween 20 was dissolved in PBS so as to attain a concentration of 0.05% (w/v).

* A solution of enzyme-labeled avidin;

To prepare the solution, peroxidase-avidin D (A-2004: Vector Co.) was diluted to 1/5000 with PBS containing 1% BSA.

* A substrate solution;

To prepare the solution, 3,3',5,5'-tetramethylbenzidine dihydrochloride (TMBZ) and aqueous hydrogen peroxide were dissolved in 0.2 M citrate buffer (pH 3.8) to attain respective concentrations of 0.3 mM and 0.005% (w/w).

* Enzyme reaction stopping solution;

1N sulfuric acid was used.

d) Standard curve

To each of wells containing an immobilized antibody reagent, PBS containing 1% BSA was added in an amount of 100 μl/well, then a standard solution of smooth muscle myosin was added thereto in an amount of 50 μl/well and the mixture was stirred and subsequently allowed to stand at room temperature for four hours. After three washings with the washing solution, the solution of biotinylated antibody (1H6) was added in an amount of 50 μl/well and the mixture was allowed to stand at room temperature for 30 minutes. After three washings with the washing solution, the solution of enzyme-labeled avidin was added in an amount of 50 μl/well and the mixture was allowed to stand at room temperature for 15 minutes. After three washings with the washing solution, the substrate solution was added in an amount of 100 μl/well and the mixture was allowed to stand at room temperature for 10 minutes to cause coloring. The enzyme reaction stopping solution was dispensed in an amount of 100 μl/well to terminate reaction, and the absorbance at 450 nm was measured with a microplate photometer. The standard curve obtained is shown in FIG. 1.

e) Cross-reactivity

Figure 2:
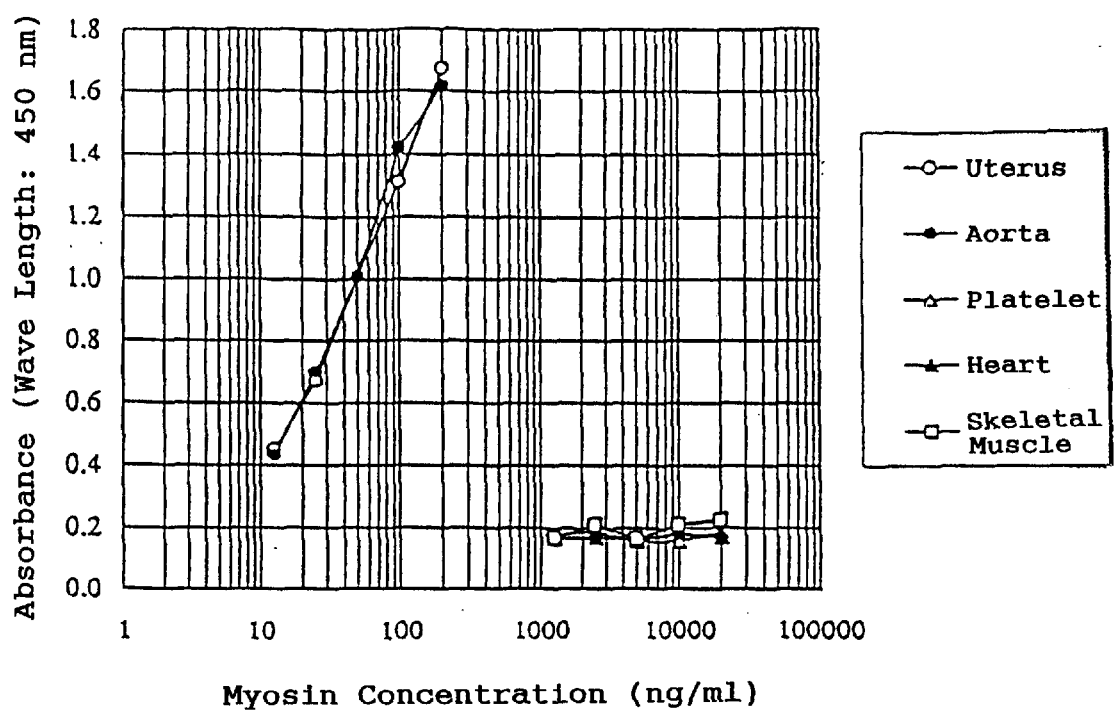
FIG. 2 shows the results of investigation on cross-reactivity.

According to the operation method described in d), cross-reactivity to various kinds of myosin was investigated. As shown in FIG. 2, it was confirmed that the antibodies had comparatively high reactivity with uterus smooth muscle myosin and aortic smooth muscle myosin but almost no reactivity with skeletal muscle myosin, heart muscle myosin, and platelet myosin.

Example 4

(Labeling of monoclonal antibodies)

A 1 mg/ml solution of anti-smooth muscle myosin imonoclonal antibody (9D7) (20 μl) and Na$^{125}$I (3.7 MBq) was mixed and a 0.3% solution of chloramine T (5 μl) was further mixed for 30 seconds with a vortex. To the mixture, a 0.5% solution of sodium pyrosulfite (10 μl), a 1% solution of potassium iodide (5 μl), and a 1% BSA solution (5 μl) were successively added and mixed. The reaction mixture was passed through a PD10 column (Pharmacia Co.) equilibrated with a 1% solution of BSA, then eluted with a 1% solution of BSA, and fractionated by 1 ml. The fractions were measured with an auto-gamma-counter and the counts of them showed two peaks. Fractions attributed to the first peak were collected to obtain a $^{125}$I anti-smooth muscle myosin monoclonal antibody.

Example 5

(Diagnostic imaging by use of a $^{125}$I anti-smooth muscle myosin monoclonal antibody)

Male rats weighing 300 g were anesthetized with pentobarbital by way of cannulation through femoral artery. A spring coil guide wire of 0.014 inch was inserted to the abdominal aorta, which was exposed and compressed with forceps to damage aorta media under operation of the guide wire. Immediately, $^{125}$I anti-smooth muscle myosin monoclonal antibody (1.23 MBq) was intravenously injected from the femoral artery and the wound was sutured.

Four or 48 hours later, some of the rats were sacrificed for removal of organs, and then the $^{125}$I counts/g of tissue were compared and autoradiographic imaging was conducted.

Figure 3:
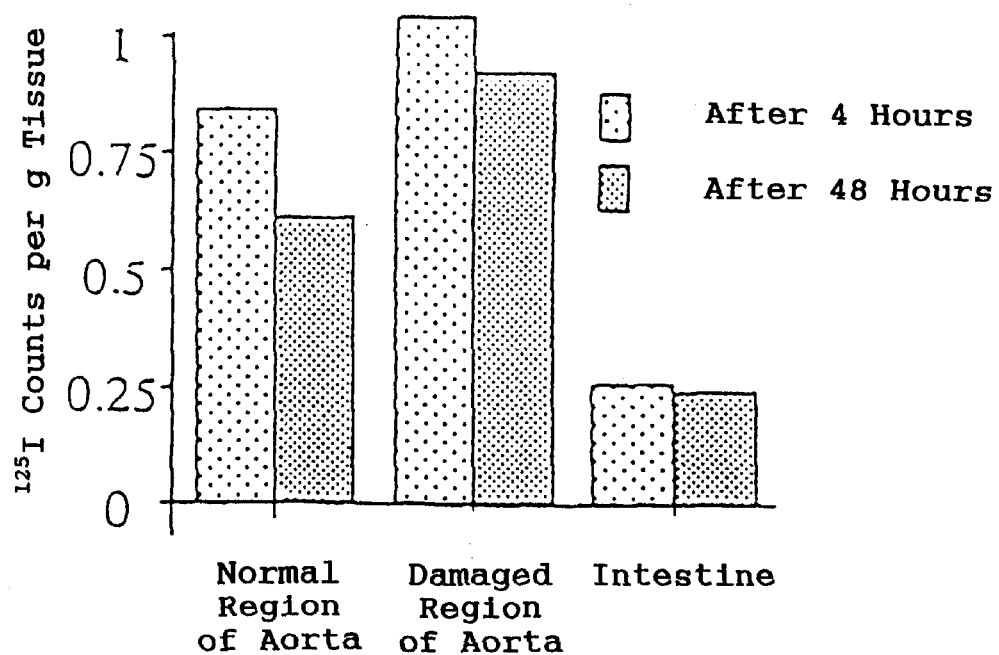
FIG. 3 shows the results of $^{125}$I counts/g tissue.

As shown in FIG. 3, the counts at the damaged part of aortas were higher than those at the non-damaged parts, both after 4 hours and after 48 hours, and this tendency was remarkable in the case of 48 hours.

Figure 4:
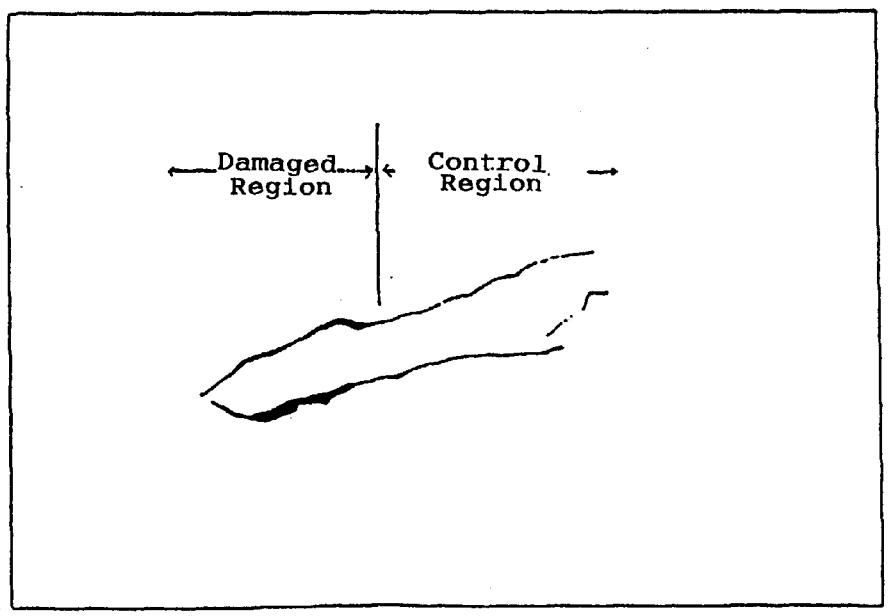
FIG. 4 shows the results of autoradiographic imaging.

As shown in FIG. 4, accumulation of $^{125}$I was observed by autoradiography in accordance with the damaged parts.

Example 6

Hybridoma 8B8 which produces a monoclonal antibody specifically reacting to human small intestine smooth muscle myosin was established in a manner similar to that described in 1) of Example 2 by use of human small intestine smooth muscle myosin instead of human uterus smooth muscle myosin. This hybridoma was deposited with the National Institute of Bioscience and Human-Technology, Agency of Industrial Science and Technology (1–3, Higashi 1 chome, Tsukuba-shi, Ibaraki-ken, 305, JAPAN) as IMH8B8 on Mar. 5, 1996 under Budapest Treaty. and was allotted an accession number FERM BP-5444 dated Mar. 5, 1996.

The monoclonal antibody produced from this hybridoma was purified by the method 2) of Example 2, and properties of the monoclonal antibody were examined by the methods described in Example 3. The results are as follows.

a) Isotype : IgG2b/κ b) Reaction specificity: Reactive with smooth muscle myosin heavy chains and not reactive with light chains.

c) Cross-reactivity: Reactive with small intestine smooth muscle myosin, uterus smooth muscle myosin, and aortic smooth muscle myosin; and not reactive with skeletal muscle myosin, heart muscle myosin, and platelet myosin (non-muscle type myosin).

d) Species specificity: Reactive with rat smooth muscle myosin and also with human smooth muscle myosin.

Next, the monoclonal antibody (8B8) was labeled by the method of Example 4, and diagnostic imaging for damaged parts of aorta was performed in a model experiment using rats in accordance with Example 5. As a result, accumulation of $^{125}$I was confirmed in the damaged parts and the image had a contrast higher than that obtained by use of a monoclonal antibody (9D7).

Example 7

(Conversion of a monoclonal antibody to a Fab antibody)

The concentration of the anti-smooth muscle myosin monoclonal antibody (IMH8B8) was adjusted with PBS to 2 mg/ml, and EDTA was added thereto so that the concentration thereof became 2 mM. The concentration of mercury papain (Sigma Co.) was adjusted to 1 mg/ml with PBS containing cystein (5 mM) and EDTA (2 mM), and the mixture was preincubated at 370 for 30 minutes. A papain solution (1 wt. % based on the amount of the antibody) was added to the antibody solution, and the mixture was incubated at 37° for 15 minutes. Iodoacetamide was added thereto so that the final concentration thereof became 5 mM to terminate the enzyme reaction. The enzyme-treated antibody solution was mixed with an equal volume of 3 M NaCl and 1.5 M glycine buffer (pH 8.9), and the mixture was passed through a Protein A Sepharose column (Pharmacia Co.) equilibrated with the above buffer to adsorb Fc contained in the antibody solution. The eluate was concentrated by ultrafiltration and then dialyzed against PBS, and the purity of Fab was confirmed by SDS-PAGE.

Example 8
(Diagnostic imaging with a $^{125}$I anti-smooth muscle myosin monoclonal Fab antibody)

IMH8B8-Fab formed in Example 7 was labeled with $^{125}$I by use of the method of Example 4. Male rats weighing 300 g were anesthetized with pentobarbital by way of cannulation through the femoral artery. A spring coil guide wire of 0.014 inch was inserted to the abdominal aorta, which was exposed and compressed with forceps to damage aorta media under operation of the guide wire. Immediately, a $^{125}$I-labeled IMH8B8-Fab antibody (1.23 MBq) was intravenously injected from a femoral artery and the wound was sutured.

One hour or 6 hours later, some of the rats were sacrificed to remove organs, and the $^{125}$I counts/g of tissue were compared and autoradiographic imaging was conducted.

Figure 5:
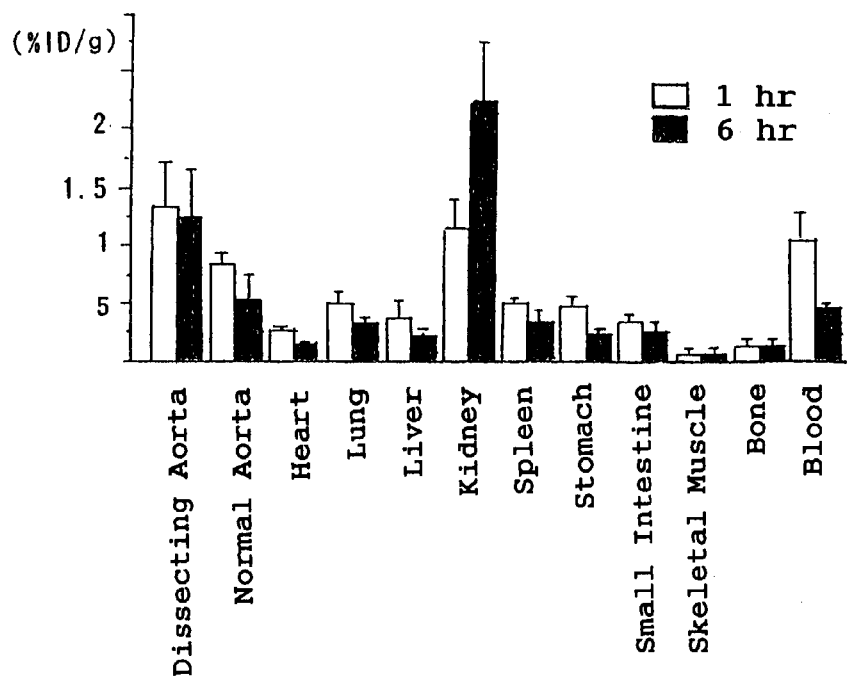
FIG. 5 shows the distribution of the anti-smooth muscle myosin antibody in rat.
Figure 6:
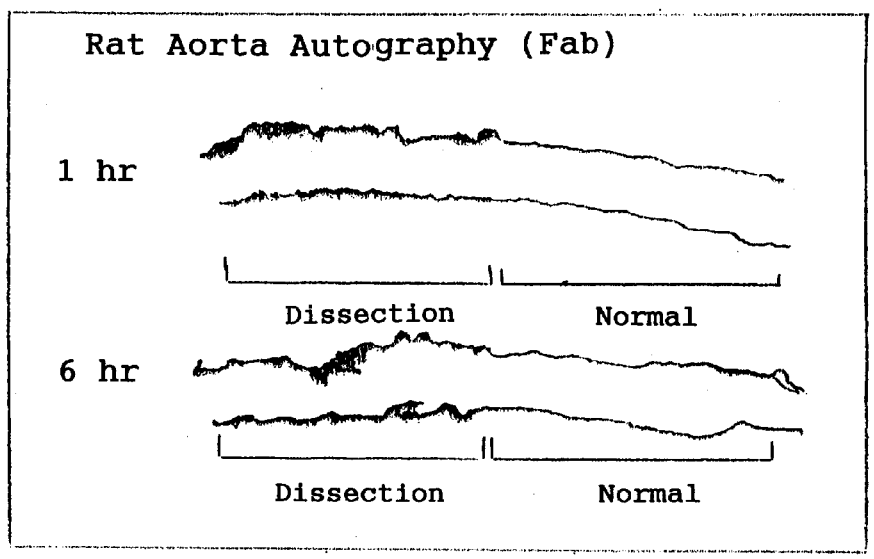
FIG. 6 shows the results of imaging by autoradiography.

The results show that the half-life in blood was remarkably improved as compared with the case in which $^{125}$I-labeled IMH8B8-IgG antibody of Example 6 was used, and that the counts in blood were less than those in the damaged region of aorta when 6 hours has elapsed after intravenous injection (FIG. 5). Similar to the case of Example 6, accumulation of $^{125}$I in accordance with the damaged regions was observed in autoradiography (FIG. 6).

The present inventors have found that accurate and specific diagnostic imaging for a region affected by the above-mentioned diseases can be performed by binding and concentrating a monoclonal antibody against human smooth muscle myosin or active fragments of the antibody labeled with a radioactive isotope, specifically to the region affected by angiopathic diseases.

Therefore, the diagnostic agent and kit of the present invention are useful for diagnostic imaging of angiopathic diseases such as dissecting aortic aneurysm or angiitis, particularly for diagnostic imaging of these diseases in an acute stage. Use of the diagnostic agent and kit has enabled the specification of the region affected by these diseases.

What is claimed is:

1. A method of diagnostic imaging and determining the pathological site of dissecting aortic aneurysm comprising:

administering a diagnostic agent to a patient, said diagnostic agent comprising a monoclonal antibody against human smooth muscle myosin, or active fragments thereof, labeled with a radioactive isotope, said antibody being (1) reactive with smooth muscle myosin heavy chains and not with smooth muscle myosin light chains, (2) reactive with smooth muscle myosin and not with skeletal muscle myosin, heart muscle myosin, or platelet myosin, and (3) reactive with both human smooth muscle myosin and rat smooth muscle myosin, and measuring radioactivity in the patient after administration and imaging the pathological site of dissecting aortic aneurysm in the patient.

2. The method according to claim 1, wherein the diagnostic agent is obtained from a kit comprising (a) a coupling compound, (b) said monoclonal antibody against human smooth muscle myosin, or active fragments thereof, and (c) a solution of a radioactive isotope.

3. A method of diagnostic imaging and determining the pathological site of angiitis comprising:

administering a diagnostic agent to a patient, said diagnostic agent comprising a monoclonal antibody against human smooth muscle myosin, or active fragments thereof, labeled with a radioactive isotope, said antibody being (1) reactive with smooth muscle myosin heavy chains and not with smooth muscle myosin light chains, (2) reactive with smooth muscle myosin and not with skeletal muscle myosin, heart muscle myosin, or platelet myosin, and (3) reactive with both human smooth muscle myosin and rat smooth muscle myosin, and measuring radioactivity in the patient after administration and imaging the pathological site of angiitis in the patient.

4. The method according to claim 3, wherein the diagnostic agent is obtained from a kit comprising (a) a coupling compound, (b) said monoclonal antibody against human smooth muscle myosin, or active fragments thereof, and (c) a solution of a radioactive isotope.

5. The method according to claim 2, wherein the coupling compound is a bifunctional chelating agent.

6. The method according to claim 4, wherein the coupling compound is a bifunctional chelating agent.

* * * * *